United States Patent [19]

Solo

[11] Patent Number: 5,129,102

[45] Date of Patent: Jul. 14, 1992

[54] CAP PROVIDED WITH REMOVABLE FLIP UP AND DOWN GLASSES

[76] Inventor: Alan J. Solo, 1835 Burnett St., Brooklyn, N.Y. 11229

[21] Appl. No.: 733,347

[22] Filed: Jul. 22, 1991

[51] Int. Cl.$^5$ .............................................. A61F 9/00
[52] U.S. Cl. .......................................... 2/10; 2/199; 2/453; 2/DIG. 6
[58] Field of Search ................ 2/10, 12, 13, 15, 196, 2/199, 209.1, 453, DIG. 6; 351/155

[56] References Cited

U.S. PATENT DOCUMENTS

| | | | |
|---|---|---|---|
| 1,709,765 | 4/1929 | Auel | 2/10 |
| 1,955,232 | 4/1934 | Gallaway | 2/10 |
| 2,026,741 | 1/1936 | Kintz | 2/10 |
| 2,467,448 | 4/1949 | Vaca | 2/10 |
| 2,475,471 | 7/1949 | Brown | 2/10 |
| 2,481,960 | 9/1949 | Wall | 2/10 |
| 2,538,608 | 1/1951 | Vaca | 2/10 |
| 2,560,669 | 7/1951 | Vaca | 2/10 |
| 2,648,091 | 8/1953 | Jones | 2/10 |
| 4,819,274 | 4/1989 | Day | 2/10 |
| 4,951,316 | 8/1990 | Moody | 2/10 |
| 5,056,164 | 10/1991 | Lisle | 2/DIG. 6 |

FOREIGN PATENT DOCUMENTS 1174669  3/1959  France .................................... 2/10

Primary Examiner—Werner H. Schroeder
Assistant Examiner—Diana L. Biefeld
Attorney, Agent, or Firm—Goodman & Teitelbaum

[57] ABSTRACT

A cap provided with removal flip up and down glasses including a mounting member for positioning the flip up and down glasses on an outwardly extending visor of the cap. Attachment members pivotally secure a pair of lenses of the flip up and down glases to the mounting member so that the glasses can be flipped up to a first position adjacent to the visor and also flipped down to a second position so that the lenses are disposed at a proper eye level for a person wearing the cap. Preferably, the lenses are removable from the attachment members. Separable fasteners are disposed between the visor and the mounting member for removably securing the visor and the mounting member together. One portion of the fasteners is secured on an underside of the visor and another mating portion of the fasteners is secured to an upper surface of the mounting member. Preferably, the mounting member is tapered so that the front edge is thicker than a rear edge thereof, where the mounting member can be fabricated from a rigid or flexible plastic material. In a modified form, a transversely disposed hinge is provided between adjacent parts of the mounting member to permit the parts to pivot relative to each other when opposite sides of the visor are folded towards each other.

21 Claims, 2 Drawing Sheets

CAP PROVIDED WITH REMOVABLE FLIP UP AND DOWN GLASSES

BACKGROUND OF THE INVENTION

The invention relates to flip up and down glasses and, more particularly, to flip up and down glasses which are removably attached to a cap, such as a baseball cap.

There are many occasions when a person wearing glasses, such as prescription glasses or sun glasses, must remove the glasses when performing certain tasks. For example, a driver wearing sun glasses must remove same for better vision when driving through a tunnel, or a person wearing sun glasses must remove same for better vision when entering a building, or a person wearing reading glasses must remove same in order to see an object at a distance.

Flip up and down glasses, particularly sun glasses of this type, are well known in the art. However, these flip up and down sun glasses can usually only be attached or clipped onto a person's regular glasses, or in some cases, the flip up and down lenses of the sun glasses are attached to the frames which must be worn by the person in the same manner that glasses are worn. Accordingly, in either case, the person must wear glasses having frames that usually rest on the person's nose and are mounted on or behind the person's ears, which could be uncomfortable.

However, the prior art devices are not particularly directed to flip up and down glasses which can be easily used by the person, so that there is presently a need for removable flip up and down glasses which can be easily attached to and removed from a cap, such as a baseball cap, which is more comfortable to wear.

SUMMARY OF THE INVENTION

It is accordingly an object of the present invention to provide a cap provided with removable flip up and down glasses which avoids the afore-mentioned problems of the prior art devices.

Another object of the present invention is to provide a cap provided with removable flip up and down glasses which includes mounting means for positioning the flip up and down glasses on an outwardly extending visor of the cap.

A further object of the present invention is to provide a cap provided with removable flip up and down glasses, as described above, which includes attachment means for pivotally securing a pair of lenses of the flip up and down glasses to the mounting means, where the lenses are detachable from the attachment means.

Still another object of the present invention is to provide a cap provided with removable flip up and down glasses, as described above, which includes separable fasteners disposed between the visor and the mounting means for removably securing the visor and the mounting means together, where one portion of the fasteners is secured on an underside of the visor and another mating portion of the fasteners is secured to an upper surface of the mounting means.

A further object of the present invention is to provide a cap provided with removable flip up and down glasses, as described above, where the mounting means is tapered so that the front edge is thicker than a rear edge thereof.

Another object of the present invention is to provide a cap provided with removable flip up and down glasses where the mounting means can be fabricated from a rigid or flexible plastic material, or in a modified form, a transversely disposed hinge can be provided between adjacent parts of the mounting means to permit the parts to pivot relative to each other when opposite sides of the visor are folded towards each other.

Yet another object of the present invention is to provide a cap provided with removable flip up and down glasses, as described above, which is inexpensive to manufacture, and which can be easily used by a wearer of the cap to flip the glasses up and down, or in the alternative, in which the flip up and down glasses can be easily removed from the cap.

Still another object of the present invention is to provide flip up and down glasses provided with a fastener attachment that can be quickly attached to a visor or peak of any cap.

Briefly, in accordance with the present invention, a cap is provided with removable flip up and down glasses including mounting means for positioning the flip up and down glasses on an outwardly extending visor of the cap, and attachment means for pivotally securing a pair of lenses of the flip up and down glasses to the mounting means so that the glasses can be flipped up to a first position adjacent to the visor and also flipped down to a second position so that the lenses are disposed at a proper eye level for a person wearing the cap. The lenses are preferably detachably removable from the attachment means.

Separable fastener means are disposed between the visor and the mounting means for removably securing the visor and the mounting means together, where one portion of the fastener means are secured on an undersurface of the visor and another mating portion of the fastener means is secured to an upper surface of the mounting means.

Preferably, the mounting means includes a mounting member which is tapered so that the front edge is thicker than a rear edge thereof, where the mounting member can be fabricated from a rigid or flexible plastic material, or in a modified form, a transversely disposed hinge can be provided between adjacent parts of the mounting member to permit the parts to pivot relative to each other when opposite sides of the visor are folded towards each other.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of preferred embodiments in which.

In the various figures of the drawings, like reference characters designate like parts.

DESCRIPTION OF THE PREFERRED EMBODIMENTS

Figure 1:
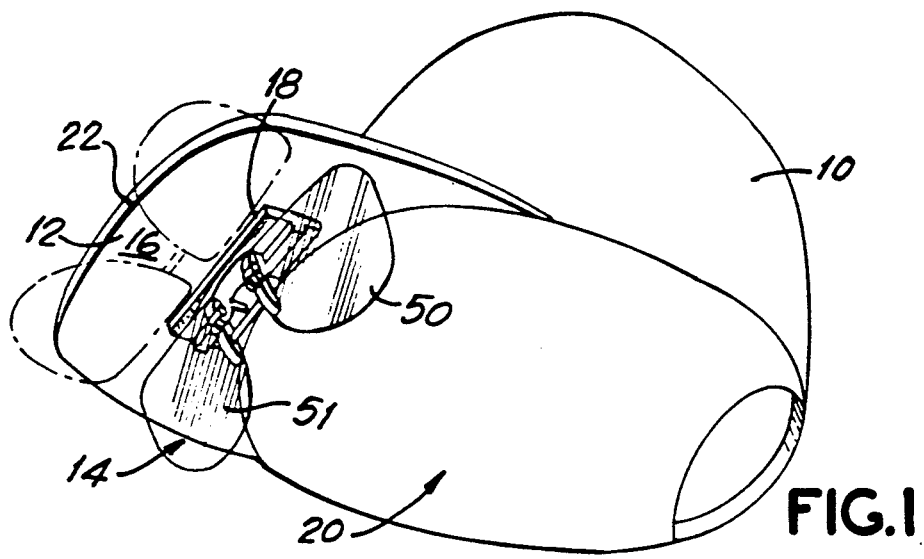
FIG. 1 is a perspective view of a baseball cap provided with removable flip up and down glasses according to the present invention.
Figure 2:
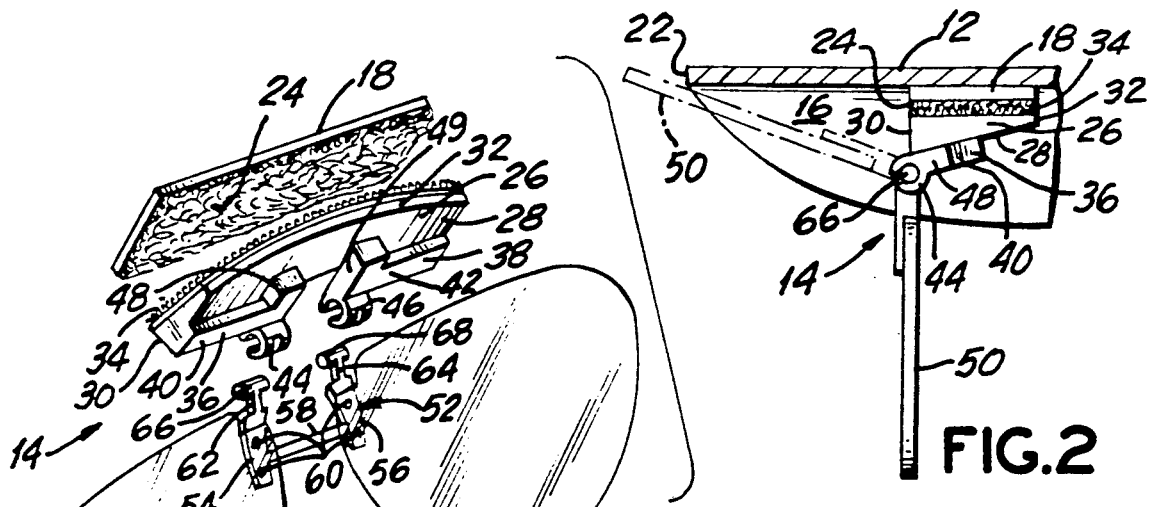
FIG. 2 is a fragmented side view, partly in section, showing the flip up and down glasses removably secured to the peak or visor of the cap.
Figure 3:
FIG. 3 is an exploded perspective view of the flip up and down glasses and the removably mounting means therefor.

Referring now to the drawings, FIG. 1 shows a conventional cap 10, such as the well known baseball cap, having an outwardly extending peak or visor 12. Flip up and down glasses 14 are removably secured to the underside 16 of the visor 12. As best shown in FIGS. 2 and 3, the upper surface of a flexible fabric strip 18 is secured by conventional means, such as an adhesive, cement, or by sewing, to a central portion of the visor 12 which is adjacent to the cap opening 20 for receiving the person's head therein. The fabric strip 18 preferably has a rectangular shape with the length thereof being disposed substantially parallel to the front edge 22 of the visor 12. One material portion 24, such as the portion containing the loops, of a Velcro Fastener is secured by conventional means to the lower surface of the fabric strip 18 facing away from the visor 12. Obviously, the fabric strip 18 and the Velcro material portion 24 could be formed as a one piece construction. The term "Velcro" is a registered trademark of the American Velcro, Inc.

The flip up and down glasses 14 includes a mounting member 26 preferably fabricated from a rigid plastic material so that the mounting member 26 has a fixed arcuate shape in its longitudinal direction. The upper surface and the lower surface 28 of the mounting member 26 are substantially rectangular in shape and are inclined relative to each other so that the front edge 30 thereof, which faces towards the visor front edge 22, being thicker than the rear edge 32 thereof, which faces towards the cap opening 20, where the reason for the taper will be explained below.

The other mating material portion 34, such as the portion containing the hooks for engaging the above-mentioned loops of the Velcro fastener is secured by conventional means to the upper surface of the mounting member 26 in order to face towards the Velcro material portion 24 on the fabric strip 18.

L-shaped attachment members 36, 38 are secured by conventional means to opposite sides on the lower surface 28 of the mounting member 26 so that the long legs 40, 42, respectively, lie adjacent to the front edge 30 thereof. C-shaped portions 44, 46 are disposed adjacent to the centrally located short legs 48, 49, respectively, so that the C-shaped portions extend beyond the front edge 30 with the openings thereof facing horizontally outwardly from the front edge 30 in the direction of the visor front edge 22.

The lenses 50, 51, such as prescription lenses or lenses for sun glasses, are secured together by an H-shaped member 52. The H-shaped member 52 includes side portions 54, 56 which are connected together by a bridge portion 58. The side portions 54, 56 are connected to the lenses 50, 51 by conventional means, such as screws or rivets 60 so that the bridge portion 58 is disposed between and separates the lenses 50, 51. At the upper ends of the side portions 54, 56 are reduced portions 62, 64 having cylindrical portions 66, 68 at the free ends thereof.

The cylindrical portions 66, 68 are removably received in the C-shaped portsions 44, 46, respectively, so that the H-shaped portion 52 with the lenses 50, 51 connected thereto are free to pivot within the C-shaped portions 44, 46 to permit the lenses 50, 51 to be flipped up and down relative to the mounting member 26. It is understood, that the short legs 48, 49 of the L-shaped members 36, 38, respectively, are spaced apart on the mounting member 26 a predetermined distance so that the cylindrical portions 66, 68 of the H-shaped member 52 can be received exactly within the C-shaped members 44, 46, respectively.

Accordingly, the fabric strip 18, with the Velcro material portion 24 thereon, is secured to the underside 16 of the cap visor 12, where the positioning thereof can be made according to the requirements of the wearer of the cap 10. The lenses 50, 51 and the H-shaped member 52 are removably, pivotally secured to the attachment members 36, 38 on the mounting member 26 which has the Velcro material portion 34 already secured on the upper surface thereof. The mounting member 26 is now positioned against the fabric strip 18 on the cap visor 12 so that the Velcro material portions 24, 34 are removably secured together in a well known manner. The person can now place the cap 10 on his head and flip the glasses 14 up and down as desired. It is noted, that if the person wishes to use the cap 10 without the glasses 14, all the person need do is remove the mounting member 26 from the fabric strip 18 so that the Velcro material portions 24, 34 are separated from each other in a well known manner.

As shown in FIG. 2, because of the thickness of the front edge 30 of the mounting member 26, the lenses 50, 51 are spaced a predetermined distance below the visor 12 so that the lenses 50, 51 are disposed at the proper eye level for the person wearing the cap 10. Furthermore, when the lenses 50, 51 are flipped up against the visor 12, as shown in phantom lines, the lenses 50, 51 are maintained in this flipped up position. It is further noted, that the tapering of the mounting member 26 positions the smaller rear edge 32 thereof closer to the visor 12 so that the rear edge 32 does not come in contact with the forehead of the person wearing the cap 10 or in contact with any glasses the person may be wearing at that time.

Figure 4:
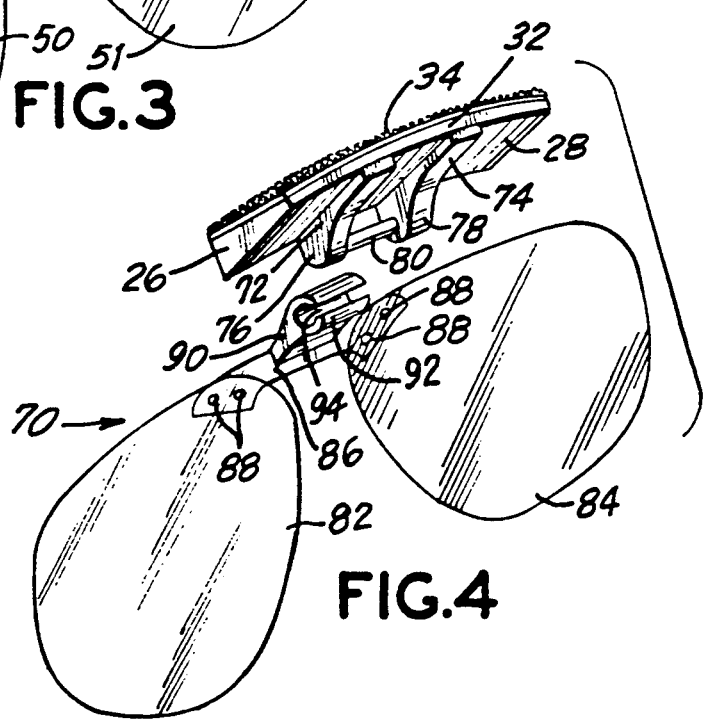
FIG. 4 is an exploded perspective view of modified flip up and down glasses.

FIG. 4 shows modified flip up and down glasses 70. In this embodiment, the tapered mounting member 26 and the mating Velcro material portion 34 are the same as mentioned above. Modified attachment members 72, 74 are secured by conventional means to the lower surface 28 of the mounting member 26 so that the ends of the arcuate enlarged portions 76, 78 thereof, respectively, lie adjacent to the front edge 30 of the mounting member 26. The attachment members 72, 74 are centrally located in the lower surface 28, and are spaced apart by a bar 80 engaged between the arcuate enlarged portions 76, 78. The bar 80 has flat surfaces along its length, the function of which will be explained below.

The lenses 82, 84, such as prescription lenses or lenses for sun glasses, are secured together by a bridge member 86. Opposite ends of the bridge member 86 are connected to the lenses 82, 84 by conventional means, such as screws or rivets 88 so that the bridge member 86 is disposed between and separates the lenses 82, 84. The bridge member 86 included a centrally disposed rearwardly extending tab portion 90 having an enlarged C-shaped portion 92 at the free rear end thereof with the opening 94 therein also facing towards the rear thereof. The enlarged C-shaped portion 92 has a selected configuration which can be mounted between the arcuate enlarged portions 76, 78 of the attachment members 72, 74, where the bar 80 is passed through the opening 94 and is removably, turnably secured in the enlarged C-shaped portion 92.

Many people when wearing a cap, prefer folding or bending the sides of the cap visor towards each other as much as possible for the appearance thereof. Accordingly, the cap visor 12 cannot be folded or bent as much as desired and still use the rigid plastic mounting member 26 set forth above. Therefore, to accomodate the desires of such people, a modified mounting member must be used.

Figure 5:
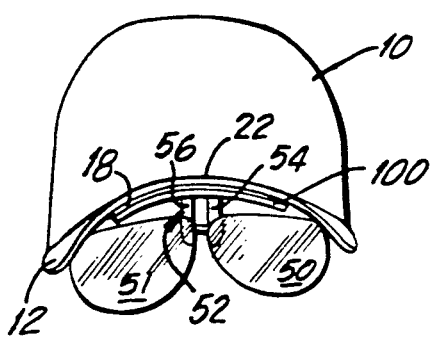
FIG. 5 is a front view of a further embodiment of the cap provided with the removable flip up and down glasses according to the present invention.
Figure 6:
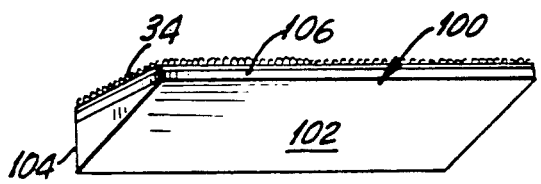
FIG. 6 is a perspective view of the mounting member of the flip up and down glasses shown in FIG. 5.

In order to solve the above-mentioned problem, FIG. 5 shows another embodiment according to the present invention using a modified mounting member 100 for the flip up and down glasses 114, shown best in FIG. 6. The mounting member 100 is fabricated from a flexible plastic material so that the opposite ends thereof can be folded or bent in towards each other, when mounted on the cap visor 12, to bend with the cap visor 12.

The upper surface and lower surface 102 of the mounting member 100 are substantially rectangular in shape and are inclined relative to each other so that the mounting member 100 is tapered, the front edge 104 thereof being thicker than the rear edge 106 thereof, for the same reasons as mentioned above with respect to the tapered mounting member 26. Here again, the mating Velcro material portion 34 is secured by conventional means to the upper surface of the mounting member 100. Furthermore, though not shown, either the L-shaped attachment members 36, 38 or the attachment members 72, 74 are secured to the lower surface 102 of the mounting member 100 in the same manner and for the same functions as mentioned above to form the flip up and down glasses 114.

Figure 8:
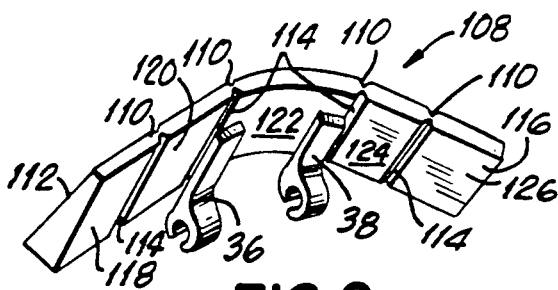
FIG. 8 is a perspective view of the modified mounting member of FIG. 7 provided with attachment members for the glasses.
Figure 9:
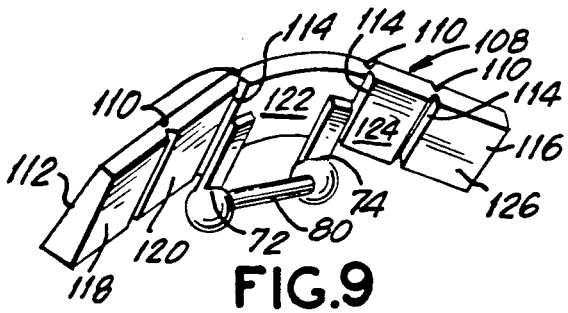
FIG. 9 is a perspective view of the modified mounting member of FIG. 7 provided with modified attachment members for the glasses.
Figure 7:
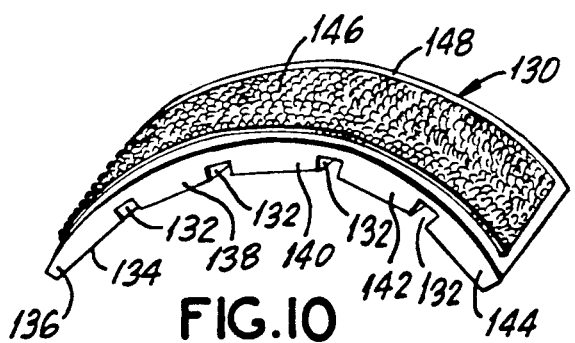
FIG. 7 is a perspective view of a modified mounting member.

FIGS. 7, 8, 9 show a further modified mounting member 108, preferably fabricated from a plastic material. Transversely extending V-shaped slots 110 are formed in the upper surface 112 and associated corresponding transversely extending V-shaped slots 114 are formed in the lower surface 116 to provide hinge means so that all the parts 118, 120, 122, 124 and 126 formed thereby can pivot relative to each other in order for the mounting member 108 to substantially bend with the cap visor 12 when mounted thereon.

Accordingly, a mating Velcro material portion 128, as mentioned above, is secured on the upper surface of each part to function in the same manner as mentioned above. Here again, the upper and lower surfaces 112, 116 of the mounting member 108 are substantially rectangular in shape and are inclined relative to each other so that the mounting member 108 is tapered as best shown in FIGS. 8 or 9, for the same reasons mentioned above. Preferably, the central part 122 is arcuate in shape and is wider in the longitudinal direction than the other parts 118, 120, 124 and 126 to accomodate the attachment means.

FIG. 8 shows the L-shaped attachment members 36, 38 attached to the lower surface 116 of the central part 122, and FIG. 9 shows the attachment members 72, 74, with the bar 80 therebetween, attached to the lower surface 116 of the central part 122.

Figure 10:
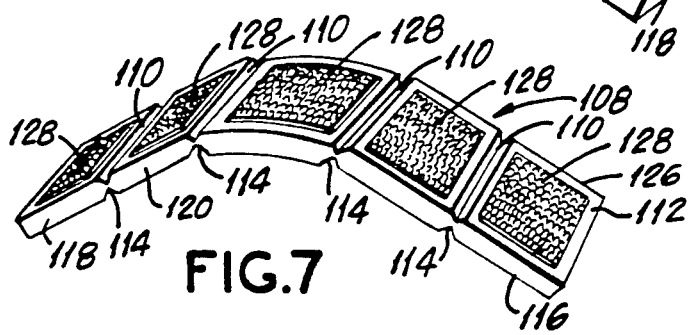
FIG. 10 is a perspective view of a further modified mounting member.

FIG. 10 shows a still further modified mounting member 130, preferably fabricated from a plastic material. Transversely extending U-shaped slots 132 are formed in the lower surface 134 to provide hinge means so that the parts 136, 138, 140, 142 and 144 formed thereby can pivot relative to each other in order for the mounting member 130 to substantially bend with the cap visor 12 when mounted thereon.

Accordingly, a mating Velcro material portion 146, as mentioned above, is secured on the upper surface 148 to function in the same manner as mentioned above Here again, the upper and lower surfaces 148, 134 of the mounting member 130 are substantially rectangular in shape and are inclined relative to each other so that the mounting member 130 is tapered in the same manner as shown in FIGS. 8 or 9, for the same reasons mentioned above. The mounting member 130 is arcuate in shape the longitudinal direction the same as the above mentioned mounting member 26.

Preferably, though not shown, either the L-shaped attachment members 36, 38 or the attachment members 72, 74 are secured to the lower surface 134 of the centrally located part 140 of the mounting member 130 in the safe manner and for the same functions as mentioned above to form the flip up and down glasses.

Figure 11:
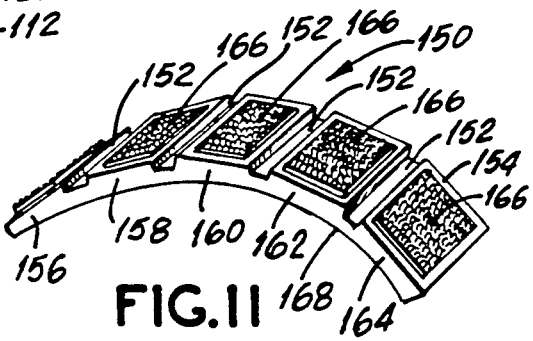
FIG. 11 is a perspective view of a still further modified mounting member.

FIG. 11 shows another modified mounting member 150, preferably fabricated from a plastic material, which is basically a reversal of the mounting member 130 shown in FIG. 10. Transversely extending U-shaped slots 152 are formed in the upper surface 154 to provide hinge means so that the parts 156, 158, 160, 162 and 164 formed thereby can pivot relative to each other in order for the mounting member 150 to substantially bend with the cap visor 12 when mounted thereon.

Accordingly, a mating Velcro material portion 166, as mentioned above, is secured on the upper surface 154 of each part 156 to 164 to function in the same manner as mentioned above. Here again, the upper and lower surfaces 154, 168 are substantially rectangular in shape and are inclined relative to each other so that the mounting member 150 is tapered in the same manner as shown in FIGS. 8 or 9, for the same reasons mentioned above. The mounting member 150 is also arcuate in shape in the longitudinal direction the same as the above mentioned mounting member 26.

Preferably, though not shown, either the L-shaped attachment members 36, 38 or the attachment members 72, 74 are secured to the lower surface 168 of the centrally located part 160 of the mounting member 150 in the same manner and for the same functions as mentioned above to form the flip u- and down glasses.

Figure 12:
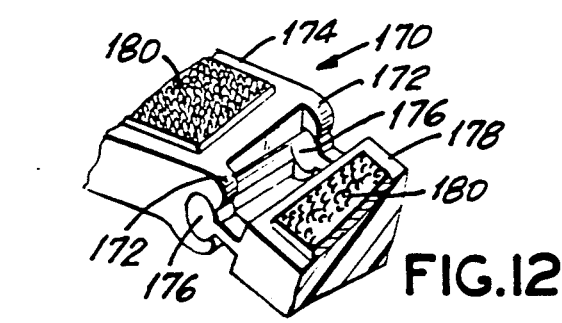
FIG. 12 is a fragmented perspective view showing the pivotal attachment of the parts of another modified mounting member.

FIG. 12 shows another modified mounting member 170 similar to the above mentioned mounting members, however the hinge means have been modified to include spaced apart C-shaped portions 172 on opposite sides of one edge of one part 174 of the mounting member 170, and spaced apart cylindrical portions 176 on opposite sides of an associated edge of an adjacent part 178 of the mounting member 170. The edge of the part 174 faces the associated edge of the adjacent part 178 so that the cylindrical portions 176 are pivotally received in the C-shaped portions 172, respectively. Here again, a mating Velcro material portion 180, as mentioned above is secured on the upper surface of each part 174, 178 to function in the same manner as mentioned above. The remaining structure of the mounting member 170 is the same as mentioned above so that a further description thereof is not thought necessary.

Figure 13:
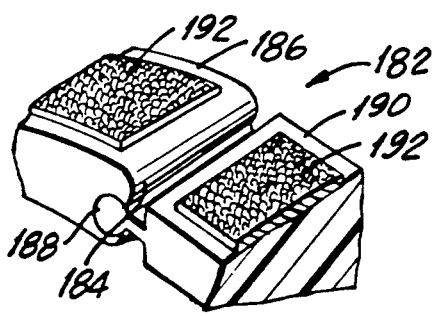
FIG. 13 is a fragmented perspective view showing the pivotal attachment of a yet further modified mounting member.

FIG. 13 shows a further modified mounting member 182 similar to the above mentioned mounting member 170 of FIG. 12, however the hinge means have been modified to include a single C-shaped portion 184 along on edge of one part 186 of the mounting member 182, and a single cylindrical portion 188 along an associated edge of an adjacent part 190 of the mounting member 182. The edge of the part 186 faces the associated edge of the adjacent part 190 so that the cylindrical portion 188 is pivotally received in the C-shaped portion 184. Once again, a mating Velcro material portion 192, as mentioned above, is secured on the upper surface of each part 186, 190 to function in the same manner as mentioned above. Here again, the remaining structure of the mounting member 182 is the same as mentioned above so that a further description thereof is not thought necessary.

Numerous alterations of the above structures herein discussed will suggest themselves to those skilled in the art. However, it is to be understood that the present disclosure relates to preferred embodiments of the invention which are for purposes of illustration only, and are not to be construed as a limitation of the invention.

What is claimed is:

1. A cap provided with removable flip up and down glasses comprising:
   said cap having an outwardly extending visor;
   mounting means for positioning said flip up and down glasses on said visor;
   said mounting means including a mounting member having a longitudinal front edge facing towards a front edge of said visor;
   said mounting member being tapered so that said front edge of said mounting member is thicker than a rear edge thereof;
   attachment means for pivotally securing a pair of lenses of said flip up and down glasses to said mounting means so that said glasses can be flipped up to a first position adjacent to said visor and also flipped down to a second position so that said lenses are disposed at a proper eye level for a person wearing said cap; and
   separable fastener means disposed between said visor and said mounting means for removably securing said visor and said mounting means together with one portion of said fastener means secured on an underside of said visor and another mating portion of said fastener means secured to an upper surface of said mounting means so that said mounting means can be removed from said visor when said one portion and said mating portion of said fastener means are separated from each other.

2. A cap provided with removable flip up and down glasses according to claim 1, wherein said mounting member is fabricated from a rigid plastic material, said mounting member having a fixed arcuate shape in a longitudinal direction.

3. A cap provided with removable flip up and down glasses according to claim 1, wherein said mounting member is fabricated from a flexible plastic material to permit said mounting member to bend with said visor.

4. A cap provided with removable flip up and down glasses according to claim 1, wherein said one portion of said fastener means contains loops, and said mating portion of said fastener means contains hooks for engaging said loops.

5. A cap provided with removable flip up and down glasses according to claim 1, wherein said attachment means includes C-shaped portions secured to said mounting means, and includes cylindrical portions secured to said lenses, said cylindrical portions being pivotally received in said C-shaped portions so that said glasses can be flipped up and down relative to said mounting means.

6. A cap provided with removable flip up and down glasses according to claim 1, wherein said attachment means includes a bar secured to said mounting means, and includes a C-shaped portion secured to said lenses, said bar being pivotally received in said C-shaped portion so that said glasses can be flipped up and down relative to said mounting means.

7. A cap provided with removable flip up and down glasses according to claim 6, wherein said bar has flat surfaces along its length to maintain said C-shaped portion and said glasses in a selected one of said first and second positions.

8. A cap provided with removable flip up and down glasses comprising:
   said cap having an outwardly extending visor;
   mounting means for positioning said flip up and down glasses said visor;
   said mounting means including a mounting member having a longitudinal front edge facing towards a front edge of said visor;
   said mounting member having hinge means transversely disposed across said mounting member to permit parts of said mounting member to pivot relative to each other when opposite sides of said visor are folded towards each other;
   attachment means for pivotally securing a pair of lenses of said flip up and down glasses to said mounting means so that said glasses can be flipped up to a first position adjacent to said visor and also flipped down to a second position so that said lenses are disposed at a proper eye level for a person wearing said cap; and
   separable fastener means disposed between said visor and said mounting means for removably securing said visor and said mounting means together with one portion of said fastener means secured on an underside of said visor and another mating portion of said fastener means secured to an upper surface of said mounting means so that said mounting means can be removed from said visor when said one portion and said mating portion of said fastener means are separated from each other.

9. A cap provided with removable flip up and down glasses according to claim 8, wherein said attachment means are secured to a central one of said parts of said mounting member.

10. A cap provided with removable flip up and down glasses according to claim 9, wherein said mounting member is tapered so that said front edge of said mounting member is thicker than a rear edge thereof.

11. A cap provided with removable flip up and down glasses according to claim 8, wherein said mounting member is tapered so that said front edge of said mounting member is thicker than a rear edge thereof.

12. A cap provided with removable flip up and down glasses according to claim 8, wherein said hinge means includes transversely extending slots in at least one surface of said mounting member.

13. A cap provided with removable flip up and down glasses according to claim 12, wherein said slots are in an upper surface of said mounting member.

14. A cap provided with removable flip up and down glasses according to claim 12, wherein said slots are in a lower surface of said mounting member.

15. A cap provided with removable flip up and down glasses according to claim 12, wherein a first set of said slots is in an upper surface of said mounting member, and a second set of said slots is in a lower surface of said mounting member so that each of said hinge means includes a first slot from said first set and a second slot from said second set.

16. A cap provided with removable flip up and down glasses according to claim 8, wherein each of said hinge means includes C-shaped portions on opposite sides of one edge of a first part of said mounting member, and cylindrical portions on opposite sides of one edge of an associated second part of said mounting member, said one edge of said first part facing said one edge of said second part so that said cylindrical portions are pivotally received in said C-shaped portions.

17. A cap provided with removable flip up and down glasses according to claim 8, wherein each of said hinge means includes a C-shaped portion along one edge of a first part of said mounting member, and a cylindrical portion along one edge of an associated second part of said mounting member, said one edge of said first part facing said one edge of said second part so that said cylindrical portion is pivotally received in said C-shaped portion.

18. A cap provided with removable flip up and down glasses according to claim 8, wherein said one portion of said fastener means contains loops, and said mating portion of said fastener means contains hooks for engaging said loops, said mating portion of said fastener means being secured to an upper surface of said mounting member.

19. Flip up and down glasses adapted to be removably secured to an article worn on a person's head, comprising:
  mounting means for positioning said flip up and down glasses on the article;
  said mounting means including a mounting member having hinge means transversely disposed across said mounting member to permit parts of said mounting member to pivot relative to each other to conform to an associated surface of the article;
  attachment means for pivotally securing a pair of lenses of said flip up and down glasses to said mounting means so that said glasses can be flipped down to a first position so that said lenses are disposed at a proper eye level for the person and also flipped up to a second position away from the person's line of sight; and
  separable fastener means disposed between the article and said mounting member for removably securing the article and said mounting member together with one portion of said fastener means being secured on the associated surface of the article and another mating portion of said fastener means being secured to said mounting member so that said mounting member can be removed from the article when said one portion and said mating portion of said fastener means are separated from each other.

20. Flip up and down glasses according to claim 19, wherein said mounting member is tapered so that one longitudinal edge of said mounting member is thicker than an opposing longitudinal edge thereof.

21. Flip up and down glasses according to claim 19, wherein one of said portions of said fastener means contains loops, and the other one of said portions of said fastener means contains hooks for engaging said loops.

* * * * *